(12) United States Patent
Lamb

(10) Patent No.: US 6,537,260 B1
(45) Date of Patent: Mar. 25, 2003

(54) SUBSTANCE APPLICATOR

(76) Inventor: Peter James Brian Lamb, 12 Clifford Road., Irene, 1675 (ZA)

( * ) Notice: Subject to any disclaimer, the term of this patent is extended or adjusted under 35 U.S.C. 154(b) by 54 days.

(21) Appl. No.: 09/680,870

(22) Filed: Oct. 6, 2000

Related U.S. Application Data

(63) Continuation of application No. PCT/IB99/00598, filed on Apr. 7, 1999.

(30) Foreign Application Priority Data

Apr. 8, 1998 (ZA) ................................................ 98/2992

(51) Int. Cl.⁷ ............................................. A61M 31/00
(52) U.S. Cl. ..................................................... 604/279
(58) Field of Search ........................ 604/514, 212–217, 604/187, 279, 275, 264

(56) References Cited

U.S. PATENT DOCUMENTS

| 1,758,082 A | * | 5/1930 | McGowan | |
| 1,991,278 A | * | 2/1935 | Heintz et al. | |
| 2,147,158 A | * | 2/1939 | Goldenthal | |
| 3,570,662 A | | 3/1971 | Polyak | 206/63.2 |
| 3,653,377 A | | 4/1972 | Rebold | 128/66 |
| 3,670,730 A | * | 6/1972 | White | |
| 4,068,662 A | * | 1/1978 | Sneider | |
| 4,217,897 A | | 8/1980 | Sneider | 128/232 |
| 4,386,607 A | * | 6/1983 | Miller | |
| 4,772,274 A | | 9/1988 | Lukacs | 604/275 |
| 4,776,848 A | | 10/1988 | Solazzo | 604/247 |
| 5,061,239 A | * | 10/1991 | Shiels | |

FOREIGN PATENT DOCUMENTS

| DE | 32 33 404 A1 | 9/1984 |
| DE | 297 20 010 U1 | 1/1998 |
| WO | WO 85/04108 | 9/1985 |

* cited by examiner

Primary Examiner—Anhtuan T. Nguyen
Assistant Examiner—Ann Y. Lam

(57) ABSTRACT

An applicator (30) for applying or delivering a substance into a body cavity includes a deformable reservoir (12) for receiving and expelling the substance. The reservoir (12) has an inlet (20) spaced from an outlet, the inlet (20) being configured to be connected to a container containing the substance. Valve means (14) is positioned in the inlet (20) to inhibit flow of the substance into the body cavity is in flow communication with the reservoir (12) through the outlet of the reservoir (12).

18 Claims, 4 Drawing Sheets

SUBSTANCE APPLICATOR

This application is a continuation of PCT Application No. PCT/IB99/00598 (WO 99/52576), filed Apr. 7, 1999, which claims priority of South African Application No. 98/2992, filed Apr. 8, 1998.

THIS INVENTION relates to a substance applicator. In particular, it relates to an applicator for applying or delivering a substance into a body cavity, and to a supply of a substance.

Various conventional applicators for delivering substances to body cavities, such as the vagina and rectum, exist. Most of these conventional applicators comprises a blunt, hollow tube or barrel into which a plunger can be inserted. All of the conventional applicators suffer from at least some of the following problems:

The applicator is of a hard and non-pliable material so there is no bend or give during insertion of the applicator into a vagina. This rigidity makes vaginal insertion more difficult and painful. Often women do not know that the vagina is angled upwards from the opening and that it is not horizontal. After inserting a leading end of the applicator through the vaginal opening in the horizontal direction, the leading end collides with the back wall of the vagina, which is painful and causes the user to think that the applicator has reached the limit of the vagina. The user then injects the substance at a too shallow depth in the vagina so that it runs out of the vagina. No stop guard is provided to limit the depth of insertion of the conventional applicators into the vagina. If the applicator is inserted to the full depth of the vagina and collides with the vaginal vault, considerable pain is caused. This lack of depth control is particularly hazardous in the case of a pregnant woman. Some conventional applicators have leading ends which flare outwards which makes it even more difficult to insert into a vagina. The leading end also often has internal threads for attachment of a tube of vaginal cream to load the applicator, with these threads accumulating vaginal discharge and organisms when the applicator is inserted. The threads are difficult to clean and the applicator is therefore unhygienic. Loading marks on applicator barrels are confusing to the patients and they often do not know which mark to fill the applicator to. Too little or too much cream may then be deposited in the vagina. Conventional applicators can only comfortably be inserted into a vagina when the woman is lying on her back with her knees flexed. It is difficult to insert the conventional applicators which is often difficult to grip and difficult to control when being inserted into a vagina.

It is an object of this invention to provide means which alleviate at least some of these problems.

In accordance with a first aspect of the invention, there is provided an applicator for applying or delivering a substance into a body cavity, the applicator including a deformable reservoir for receiving and expelling the substance, the reservoir having an inlet spaced from an outlet, the inlet being configured to be connected to a container containing the substance;

valve means positioned in the inlet to inhibit flow of the substance from the reservoir through the inlet; and an elongate nozzle having an outlet for delivering the substance into the body cavity, the nozzle being in flow communication with the reservoir through the outlet of the reservoir.

An angle between a centrally disposed longitudinal axis of the nozzle and a centrally disposed axis through the inlet may be between 170° and 135°.

According to a second aspect of the invention, there is provided an applicator for applying or delivering a substance into a body cavity, the applicator including a deformable reservoir for receiving and expelling the substance, the reservoir having an inlet spaced from an outlet; and an elongate nozzle having an outlet for delivering the substance into the body cavity, an angle between a centrally disposed longitudinal axis of the nozzle and a centrally disposed axis through the inlet being between 170° and 135°.

The applicator according to the second aspect of the invention may include valve means positioned in the inlet to inhibit flow of the substance from the reservoir through the inlet.

The reservoir and the nozzle may be integrally moulded from a synthetic plastics or polymeric material, such as a silicone rubber.

The reservoir may be resiliently deformable. The reservoir may be in the form of a hollow bulb or may be spindle shaped and walls of the reservoir may contain integral reinforcing ribs to provide the reservoir with some degree of integrity.

According to a third aspect of the invention, there is provided an applicator for applying or delivering a substance into a body cavity, the applicator including a resiliently deformable reservoir for receiving and expelling the substance, the reservoir having an inlet; and an elongate nozzle, the reservoir and the nozzle being integrally moulded of a synthetic plastics or polymeric material and being arranged such that an angle between a centrally disposed longitudinal axis of the nozzle and a centrally disposed axis through the inlet is between 170° and 135°.

Preferably, the angle between the centrally disposed longitudinal axis of the nozzle and the centrally disposed axis through the inlet is between 160° and 140°, and most preferably between 155° and 145°.

The applicator according to the third aspect of the invention may include valve means positioned in the inlet to inhibit flow of the substance from the reservoir through the inlet.

The nozzle may be generally penile-shaped. A discharge end portion of the nozzle remote from the reservoir, generally may have the shape of a glans penis. Thus, the nozzle may have a rounded point which flares back like the corona of a glans penis and which in use lifts the opposing vaginal walls apart when the nozzle is inserted. The nozzle may thus have a generally triangular cross-section similar to that of a penis to allow the smallest area of contact or friction with a posterior vaginal wall. Side walls of the nozzle are thus in use angled away from lateral walls of the vagina, with a relatively broad superior wall of the nozzle being stabilized by low pressure contact with the anterior vaginal wall.

The inlet of the reservoir may include an internally threaded port.

The outlet of the nozzle may be in the form of a slit extending between opposed sides of the nozzle and may be located in an upper half of the discharge end portion of the nozzle.

Preferably, at least the nozzle is transparent or translucent. More preferably, the reservoir is also transparent or translucent.

The nozzle may be of a material having a Shore A hardness between 40 and 80, e.g. 70.

The nozzle may have a length of between 60 mm and 80 mm and a maximum external diameter of between 10 mm and 20 mm, e.g. 17 mm.

According to a fourth aspect of the invention, there is provided a supply of a substance to be delivered into a body cavity, which includes a container containing the substance and having an outlet, and an applicator as hereinbefore described, the outlet of the container being connectable or connected to the inlet of the reservoir of the applicator.

The substance may be a medicament. A difference in an internal volume of the reservoir when non-deformed and when deformed between the fingers of a user may substantially correspond to a unit dose volume of the medicament.

The substance may be any cream or gel or ointment. The substance may be intended to be delivered into the vagina of a human female. The substance may thus be a biocide, an antiseptic, an anti-fungal agent, a spermicide or a lubricant. Thus, it may be a biocidal or biostatic cream or gel or ointment. It is typically a non-aqueous or viscous cream or ointment which adheres to the vaginal epithelia.

The applicator of the invention is particularly suited for applying a non-aqueous biocidal or biostatic cream or ointment to the vaginal epithelia to inhibit the transmission of sexual diseases during sexual intercourse or for the treatment of vaginal infection.

The applicator of the invention may be sold separately from a source of the substance in which case it may be sterilized and sealed in a protective wrapping which is opened by the user. The user then couples the applicator to the source of the substance. Alternatively, the applicator may be sold as part of a supply of a substance in accordance with the invention. The supply of the substance may then also be sealed in a protective wrapping.

The invention will now be described, by way of example, with reference to the accompanying diagrammatic drawings in which FIG. 1 is a side view of an embodiment of an applicator in accordance with the invention;

Figure 1:
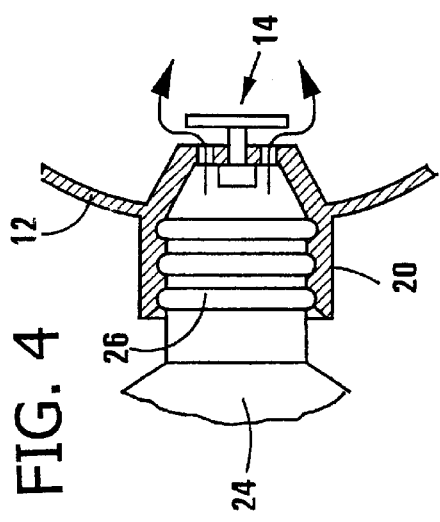
Figure 3:
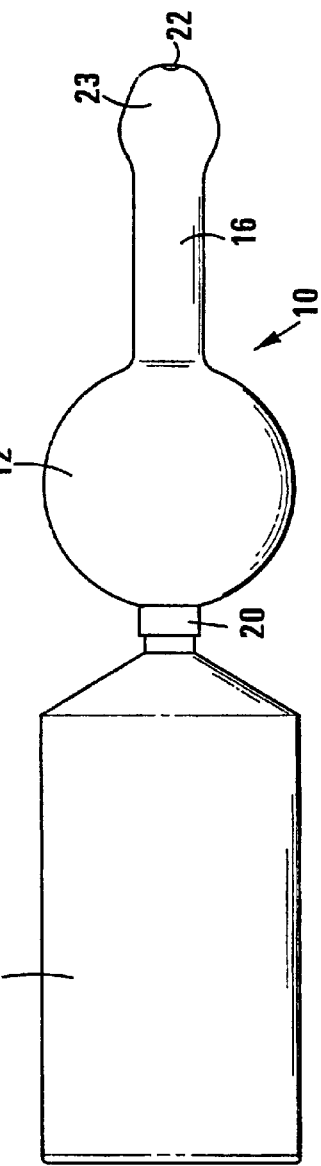
FIG. 3 is a side view of a supply of a substance to be delivered into a body cavity in accordance with the invention which includes the applicator of FIG. 1.
Figure 4:
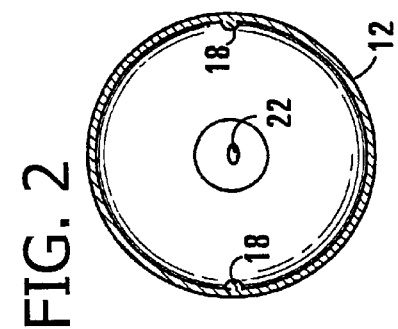
FIG. 4 is an enlarged sectioned view of an inlet of the reservoir of the applicator of FIG. 1.
Figure 5:
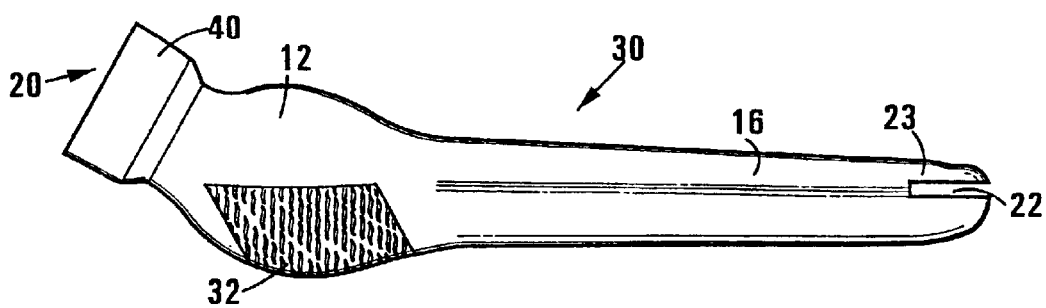
FIG. 5 is a side view of another embodiment of an applicator in accordance with the invention.
Figure 6:
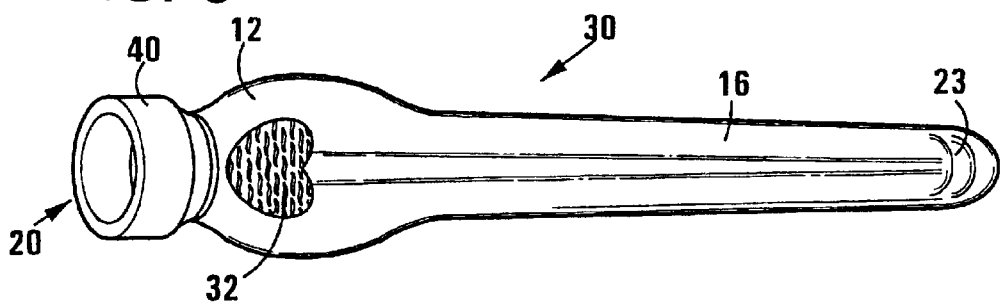
FIG. 6 is a top plan view of the applicator of FIG. 5.
Figure 7:
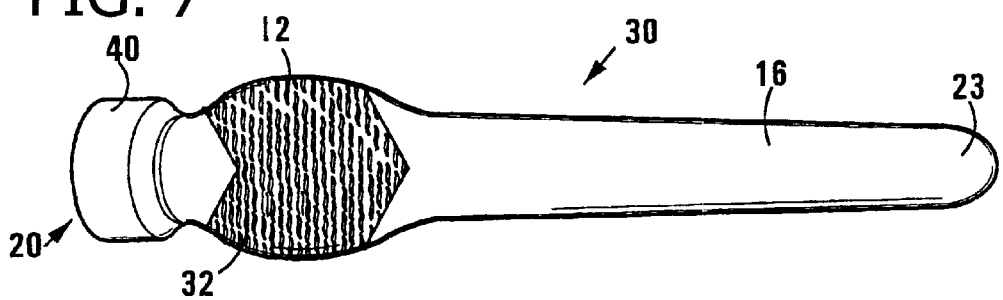
FIG. 7 is a bottom plan view of the applicator of FIG. 5.
Figure 8:
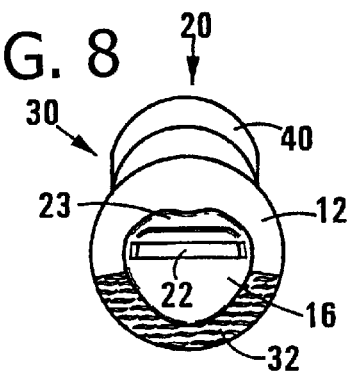
FIG. 8 is a front end view of the applicator of FIG. 5.
Figure 9:
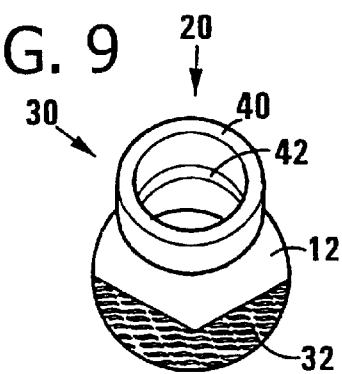
FIG. 9 is a rear end view of the applicator of FIG. 5.
Figure 10:
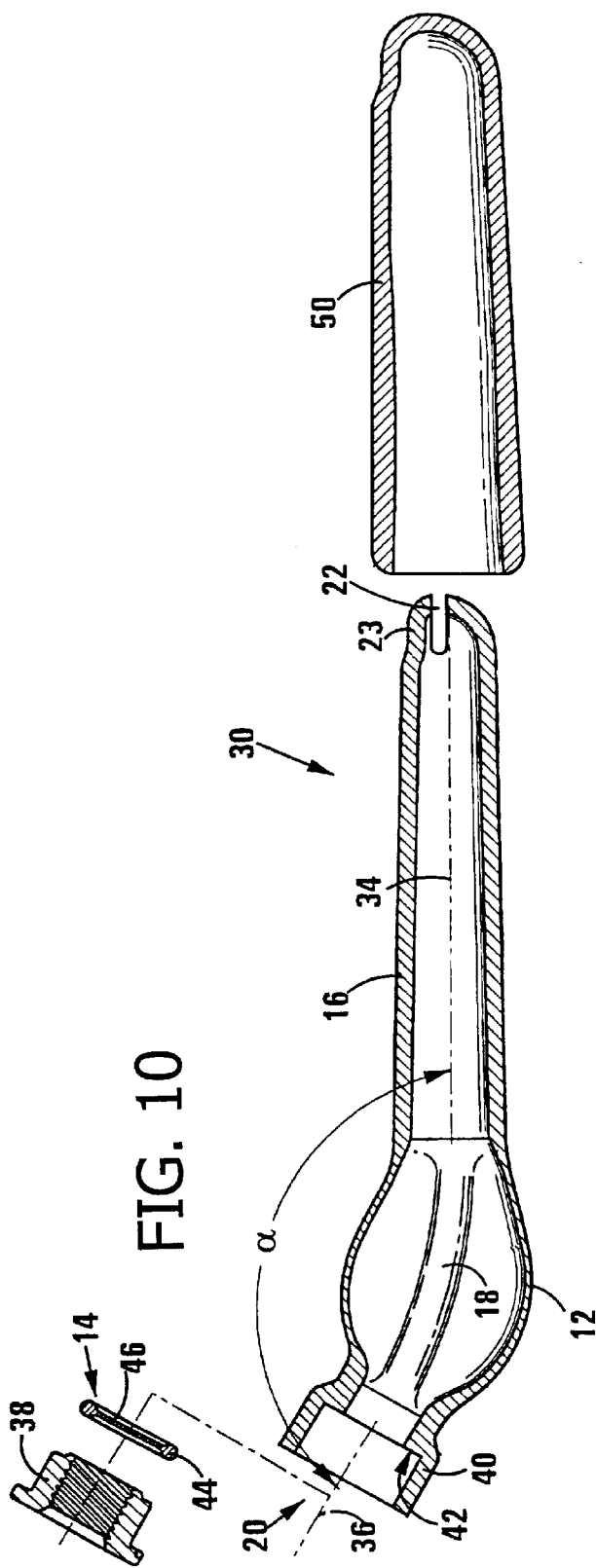
FIG. 10 is a sectioned, exploded side view of the applicator of FIG. 5, but also showing an insert, a flap valve and a cap.
Figure 11:
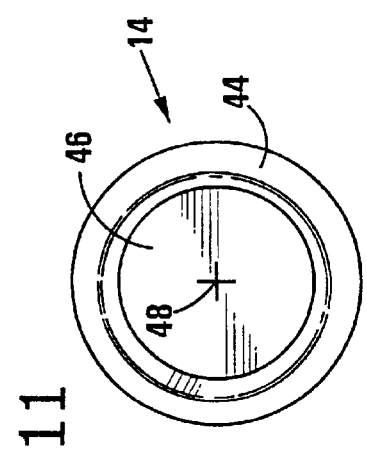
FIG. 11 is an enlarged plan view of the flap valve shown in FIG. 10.
Figure 12:
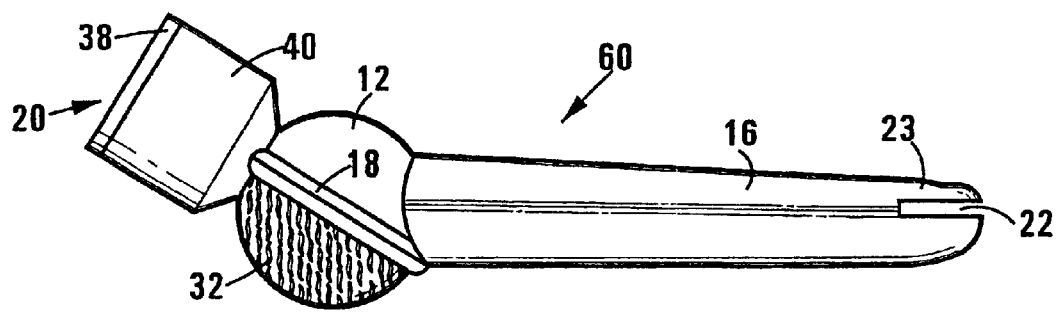
FIG. 12 is a side view of a further embodiment of an applicator in accordance with the invention.
Figure 13:
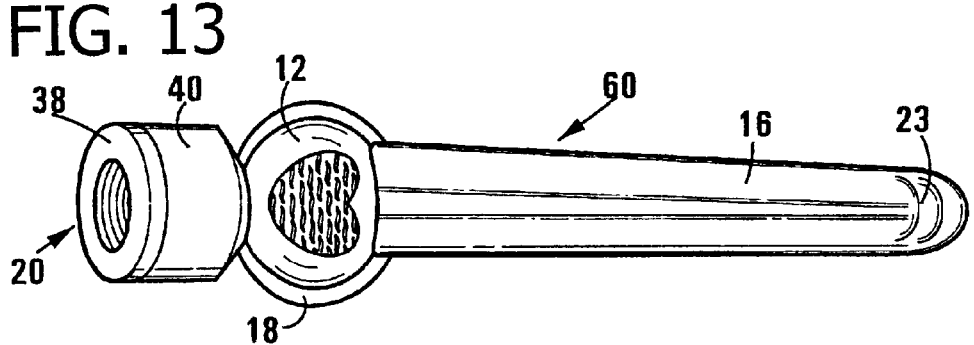
FIG. 13 is a top plan view of the applicator of FIG. 12.
Figure 14:
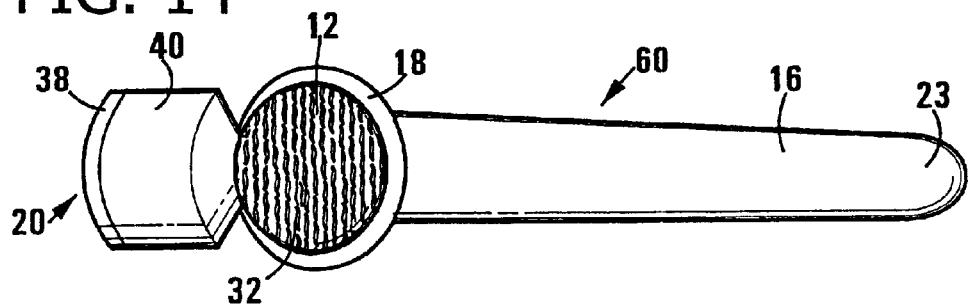
FIG. 14 is a bottom plan view of the applicator of FIG. 12.
Figure 15:
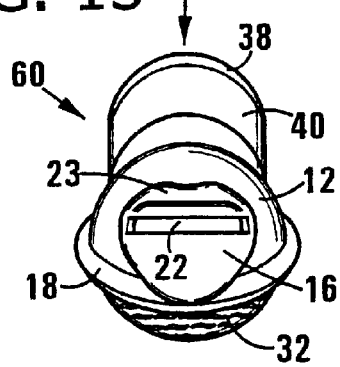
FIG. 15 is a front end view of the applicator of FIG. 12.
Figure 16:
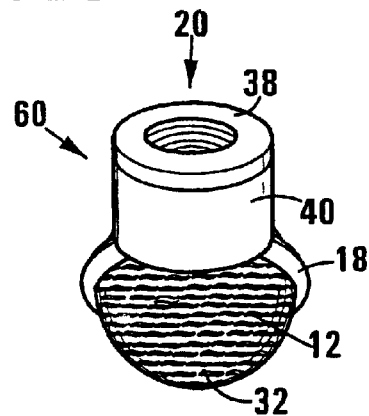
FIG. 16 is a rear end view of the applicator of FIG. 12.

Referring to FIGS. 1 and 3 of the drawings, reference numeral 10 generally indicates an embodiment of an applicator in accordance with the invention. The applicator 10 includes a flexible or deformable translucent reservoir 12 for receiving and expelling a substance to be delivered into a body cavity, valve means 14 (see FIG. 4) and an elongate translucent nozzle 16 for delivering the substance into the body cavity.

Figure 2:
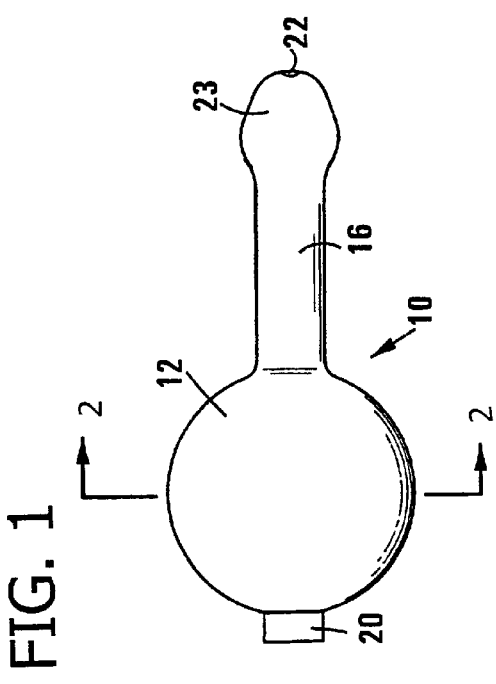
FIG. 2 is a sectioned rear end view of a reservoir of the applicator of FIG. 1, taken at ll—ll in FIG. 1.

The reservoir 12 and the elongate nozzle 16 are integrally moulded from a synthetic plastics or polymeric material such as a silicone rubber (Tufel 94005) and has a Shore A hardness of about 70. The reservoir 12 is in the form of a bulb and is resiliently deformable. It includes a pair of opposed internal reinforcing ribs 18 (see FIG. 2) providing it with a degree of integrity.

The reservoir 12 has an inlet 20 which is internally threaded. The nozzle 16 has an outlet 22 remote from the reservoir 12. An end portion 23 of the nozzle 16 remote from the reservoir 12 resembles at least to some extent a glans penis. The nozzle 16 is approximately 70 mm long and an intermediate portion of the nozzle 16 between the end portion 23 and the reservoir 12 has an external diameter of about 17 mm.

The applicator 10 is particularly, through not necessarily exclusively suitable for use as a vaginal applicator. In use, the applicator 10 is connected to a container 24 containing a substance to be delivered into a body cavity, to form a supply of a substance to be delivered into the body cavity in accordance with the invention, and as shown in FIG. 3 of the drawings.

The reservoir 12 is dimensioned such that a difference in an internal volume of the reservoir 12 when non-deformed and when deformed between the fingers of a user substantially corresponds to a unit dose volume of the substance.

The container 24 is in the form of a deformable tube having an externally threaded outlet 26 which is screw-threadedly connected to the inlet of the reservoir 12. Thus, the external thread of the outlet 26 is complemental to the internal thread of the inlet 20. The container 24 is then squeezed to deliver sufficient of the substance to fill the reservoir 12 and the nozzle 16. The substance is typically a vaginal cream, an ointment or a lubricant. The nozzle 16, or at least the end portion 23 thereof, is finger lubricated using a small amount of the substance expelled through the outlet 22. The nozzle 16 is then inserted into a body cavity, which is typically the vagina of a human female until the reservoir 12 prevents deeper insertion thereof. The container 24 affords a large comfortable grip for one hand whilst the fingers of the other hand guide the nozzle 16 to the vaginal opening. Whilst the hand holding the container 24 in a comfortable natural horizontal position supports the applicator 10 in the vagina the opposing thumb and first two fingers of the other hand compress or deform the reservoir 12 between them and so expel the contents of the reservoir 12 through the outlet 22, thus delivering it into the vagina, whereafter the nozzle 16 is withdrawn from the vagina.

The applicator 10 is left connected to the container 24. The nozzle 16 is wiped clean using a face cloth, soap and warm water. The cap 50 is positioned over the nozzle 16 to protect it from dirt or dust contamination during storage until the applicator 10 is needed to deliver the next dose of the substance. When the next dose of the substance needs to be delivered the reservoir 12 is refilled with the substance by squeezing the substance from the container 24 and the whole procedure for depositing the substance in the vagina is repeated.

In one embodiment of the invention, the nozzle 16 has an internal volume which corresponds to a unit dose volume of the substance. When the container 24 is eventually emptied and the reservoir 12 is compressed to eject the last dose of substance from the reservoir 12, a last dose of substance remains in the nozzle 16. This last dose of substance remaining in the nozzle 16 represents a significant wastage should it not also be deposited in the vagina. In this embodiment, a separate simple plastic plunger is provided (not shown to avoid this wastage. The user cuts the inlet 20 of the reservoir 12 with a pair of scissors and the nozzle 16 is inserted into the vagina. The plastic plunger is introduced into the nozzle 16 through the reservoir 12 and advanced along the length of the nozzle 16 towards the outlet 22. The residual substance in the nozzle 16 is thus injected into the vagina and the last dose of substance is used.

The valve means 14 inhibits flow of the medicament from the reservoir 12 through the inlet 20 when the reservoir 12 is being deformed, and thus acts as a non-return valve. The valve means 14 may be of the type shown in FIG. 4, but other suitable valve means, such as a ball valve, or flap valve, may also be used.

As will be appreciated, the applicator of the invention may be used to deposit any kind of vaginal cream in the vagina. A special model may be marketed for placing hormonal cream in old post-menopausal patients. The lining of the vagina in post-menopausal patients is atrophic, i.e. very thin and susceptible to non-specific bacterial infection which causes marked tenderness of the lining. The vagina is narrowed and shortened in the post-menopausal patient. These patients with dimmed vision and arthritic fingers are very prone to hurt themselves severely while struggling to insert a conventional vaginal applicator. Only 1 g to 2 g of hormonal cream needs to be deposited so a special version of the applicator (not shown) with a reservoir volume of 2 ml and a nozzle length of only 4 cm can be provided for them.

Referring to FIGS. 5 to 10 of the drawings, reference numeral 30 generally indicates another embodiment of an applicator in accordance with the invention. The applicator 30 is similar to the applicator 10, and unless otherwise indicated, the same reference numerals used above with reference to the applicator 10 are used for the same or similar parts or features.

Unlike the reservoir 12 of the applicator 10, the reservoir 12 of the applicator 30 is spindle shaped. Roughened gripping surfaces 32 are provided on an external top surface and an external bottom surface of the reservoir 12.

An angle a between a centrally disposed longitudinal axis 34 (see FIG. 10) of the nozzle 16 and a centrally disposed axis 36 through the inlet 20 is 150°.

The nozzle 16 is generally penile shaped and the discharge end portion 23 of the nozzle 16 remote from the reservoir 12 generally has the shape of a glans penis. A bottom surface of the end portion 23 has a sled-like curve in side view to inhibit abrasion of the posterior vaginal wall. The outlet 22 of the nozzle 16 is in the form of a slit extending between opposed sides of the nozzle 16 and is located in an upper half of the discharge end portion 23 of the nozzle 16, to avoid scraping vaginal exudate into the outlet 22.

The inlet 20 of the applicator 30 includes an insert 38 (only shown in FIG. 10 of the drawings), which fits with a friction fit into an inlet stub 40. The insert 38 may be mechanically or adhesively attached to the inlet stub 40. The insert 38 is typically of nylon, ABS or polypropylene and is internally threaded, thus providing the inlet 20 with an internally threaded port.

The valve means 14 is in the form of a flap or membrane valve which is sandwiched between the insert 38 and an annular shoulder 42 of the inlet stub 40. The valve means 14 includes a ring frame 44 spanned by and integrally moulded with a membrane 46 which has a centrally located aperture in the form of a cross 48. The valve means 14 is of a silicone rubber. The membrane 46 may be dome shaped to improve its working.

The applicator 30 also includes a cap 50 for the nozzle 16. The cap 50 is only shown in FIG. 10 of the drawings.

The applicator 30 is used in similar fashion to the applicator 10.

Referring to FIGS. 12 to 16 of the drawings, reference numeral 60 generally indicates a further embodiment of an applicator in accordance with the invention. The applicator 60 is similar to the applicators 10, 30 and unless otherwise indicated, the same reference numerals used above in relation to the applicators 10, 30 are used to indicate the same or similar parts or features.

Unlike the apparatus 10, 30, the applicator 60 has an external reinforcing rib 18. In FIGS. 12 to 16 of the drawings, the applicator 16 is shown with its insert 38.

The applicator 60 is used in the same fashion as the applicators 10, 30.

The Applicant believes that each of the applicators 10, 30, 60 of the invention, as illustrated, and particularly when intended as a vaginal applicator, has at least some of the following advantages:

The length of the nozzle 16 is not intimidating, but nonetheless provides effective depth of deposition of vaginal cream so that the cream does not run out of the vagina. The nozzle 16 is of a relatively soft, elastic material which is less difficult and painful to insert than the nozzle of conventional vaginal applicators. The material is easier for the fingers to grip securely and the grippability of the applicator is further improved by the gripping surfaces 32. The generally triangular, penile-like cross-section of the nozzle 16 (see FIGS. 8 and 15) is easier and more comfortable to insert into a vagina. Friction against the back vaginal wall is reduced.

The angular mounting of the nozzle 16 relative to the inlet 20, and thus to the container or tube of vaginal cream promotes easier advancement of the nozzle 16 up the vagina. There is a built-in correction for the direction or inclination of the vaginal cavity, which causes less damage and discomfort to the user. The nozzle 16 can be inserted whilst the user is sitting or standing and the procedure is therefor much easier and more comfortable to accomplish physically and much less an affront to the female's dignity.

The glans penis-like end portion 23 of the nozzle 16 is easier and more comfortable to insert than the leading end portions of conventional vaginal applicators. The shape and location of the outlet 22 of the nozzle 16 provides for better hygiene and promotes comfort when the nozzle 16 is inserted into a vagina, by eliminating any scraping effect on the back wall of the vagina.

The reservoir 12 ensures automatic depth control when the nozzle 16 is inserted into a vagina. It also ensures that a correctly metered unit dose of the substance is applied when the applicator of the invention is used. This enhances therapeutic effectiveness of the substance in the case of a medicament and reduces wastage of the substance. Furthermore, there are no confusing metering marks on the applicator.

The integrally moulded design of the reservoir 12 and the nozzle 16 provides the applicator with a degree of flexibility, which enhances comfort and ease when the nozzle 16 is inserted into a vagina.

The translucent construction of the reservoir 12 and the nozzle 16 allows a user to see and displace any air bubbles inside the applicator. This ensures complete filling of the applicator with the substance and eliminates the risk of air embolism from squirting air under pressure into the vagina, which is especially dangerous in the case of a pregnant woman. Wastage of the substance is eliminated, and the user can visually monitor the passage of the substance up the nozzle 16 and stop squeezing the tube or container when the nozzle 16 is precisely filled. There is thus no accidental overshoot of the substance out of the applicator whilst the applicator is being filled. Preferably, once the applicator has been connected to a tube or container of medicament, it should not be removed again until the tube or container is empty. This permanent mount of the applicator to the container promotes better hygiene.

The tube or container of the substance functions as a large comfortable handle for the applicator of the invention. This affords a secure grip and therefor better control of the applicator during insertion of the nozzle into the vagina.

The cap 50 for the nozzle 16 ensures that the substance inside the nozzle 16 does not dry out and prevents contamination of the nozzle 16.

What is claimed is:

1. A vaginal applicator for applying or delivering an accurate dose of a viscous vaginal medicament into a vagina, the applicator including a reservoir for filling with an accurate dose of the viscous medicament and being connectable to a multi-dose supply of the viscous medicament, the reservoir having an inlet spaced from an outlet and being configured to be deformed by the fingers of a user to expel the dose of the viscous medicament therefrom; and an elongate nozzle having an outlet for delivering the viscous medicament into the vagina, the outlet of the nozzle being in flow communication with the reservoir by means of a passage extending between the outlet of the nozzle and the outlet of the reservoir, an angle between a centrally disposed longitudinal axis of the nozzle and a centrally disposed axis through the inlet being between 170° and 135°.

2. A vaginal applicator as claimed in claim 1, which includes valve means positioned in the inlet of the reservoir to inhibit flow of the viscous medicament from the reservoir through its inlet when the reservoir is deformed by the fingers of a user.

3. A vaginal applicator as claimed in claim 1, in which the angle between the centrally disposed longitudinal axis of the nozzle and the centrally disposed axis through the inlet is between 155° and 145°.

4. A vaginal applicator as claimed in claim 1, in which the nozzle is generally penile-shaped, having a generally triangular cross section similar to that of a penis.

5. A vaginal applicator as claimed in claim 1, in which the reservoir and the nozzle are integrally moulded from a synthetic plastics or polymeric material, providing the applicator with a degree of flexibility.

6. A vaginal applicator as claimed in claim 1, in which the reservoir is resiliently deformable.

7. A vaginal applicator as claimed in claim 1, in which the inlet of the reservoir includes an internally threaded port.

8. A vaginal applicator as claimed in claim 1, in which a discharge end portion of the nozzle remote from the reservoir, generally has the shape of a glans penis with a gently curved outer surface.

9. A vaginal applicator as claimed in claim 1, in which at least the nozzle is transparent.

10. A vaginal applicator as claimed in claim 1, in which the nozzle is of a material having a Shore A hardness between 40 and 80.

11. A vaginal applicator as claimed in claim 1, in which the nozzle has a length of between 60 mm and 80 mm and a maximum external diameter of between 10 mm and 20 mm.

12. A vaginal applicator as claimed in claim 1, in which the outlet of the nozzle is in the form of a slit extending between opposed sides of the nozzle across a front of the nozzle.

13. A vaginal applicator as claimed in claim 1, in which the outlet of the nozzle is provided in a leading end of the nozzle such that the applicator can deliver the substance in front of the nozzle into the vagina.

14. A supply of a viscous vaginal medicament to be delivered into a vagina, the supply including a container sized and shaped for containing multiple doses of the viscous medicament and having an outlet, and a vaginal applicator as claimed in claim 1, the outlet of the container being connectable or connected to the inlet of the reservoir of the vaginal applicator.

15. A supply of a viscous vaginal medicament as claimed in claim 14, in which a difference in an internal volume of the reservoir when non-deformed and when deformed by the fingers of a user substantially corresponds to a unit dose volume of the medicament.

16. A supply of a viscous vaginal medicament as claimed in claim 14, in which the medicament is intended to be delivered into the vagina of a human female with the purpose of adhering to the vaginal epithelia.

17. A vaginal applicator as claimed in claim 1, in which the nozzle is directly connected to the reservoir.

18. A vaginal applicator as claimed in claim 1 wherein the reservoir is sized and shaped for receiving a single dose of viscous medicament from the multi-dose supply.

* * * * *